United States Patent
Krotoski

(10) Patent No.: US 8,864,679 B2
(45) Date of Patent: Oct. 21, 2014

(54) CUTANEOUS SENSORY DETECTION

(75) Inventors: Judith A. Bell Krotoski, Baton Rouge, LA (US); John Bell, IV, legal representative, Gonzales, LA (US)

(73) Assignee: John A. Bell, IV, Gonzales, LA (US)

( * ) Notice: Subject to any disclaimer, the term of this patent is extended or adjusted under 35 U.S.C. 154(b) by 1087 days.

(21) Appl. No.: 11/975,750

(22) Filed: Oct. 19, 2007

(65) Prior Publication Data
US 2009/0105606 A1   Apr. 23, 2009

(51) Int. Cl.
| F21V 19/00 | (2006.01) |
| F21V 33/00 | (2006.01) |
| G02B 6/00 | (2006.01) |
| A61B 19/00 | (2006.01) |
| A61B 10/00 | (2006.01) |
| A61B 5/00 | (2006.01) |

(52) U.S. Cl.
CPC .................................. *A61B 5/4827* (2013.01)
USPC ............................ 600/557; 362/572; 362/577

(58) Field of Classification Search
USPC .......................... 600/552, 553, 557; 132/329; 362/577–579, 572
See application file for complete search history.

(56) References Cited

U.S. PATENT DOCUMENTS

| 2,242,536 | A * | 5/1941 | Montgomery ................ 362/578 |
| 2,704,539 | A | 3/1955 | Fisher |
| 3,074,395 | A | 1/1963 | Kevorkian |
| 3,662,744 | A | 5/1972 | Low et al. |
| 3,933,148 | A | 1/1976 | Wyler et al. |
| 4,313,446 | A | 2/1982 | Kanatani |
| 4,823,806 | A | 4/1989 | Bajada |
| 5,027,828 | A | 7/1991 | Kovacevic et al. |
| 5,316,011 | A * | 5/1994 | Weinstein et al. ............ 600/557 |
| 5,381,806 | A | 1/1995 | Weinstein et al. |
| 5,492,132 | A | 2/1996 | Weinstein et al. |
| 5,813,855 | A * | 9/1998 | Crisio, Jr. ........................ 433/29 |
| 5,823,969 | A | 10/1998 | Christy |
| 6,234,976 | B1 * | 5/2001 | Linden .......................... 600/557 |
| 6,234,977 | B1 | 5/2001 | Christy |
| 6,364,500 | B1 * | 4/2002 | McCalla et al. .............. 362/120 |
| 6,387,055 | B1 | 5/2002 | Christy |
| 6,406,436 | B1 * | 6/2002 | Schiffman .................... 600/557 |
| 7,410,283 | B2 * | 8/2008 | West et al. .................... 362/573 |
| 2003/0104340 | A1 * | 6/2003 | Clemans ....................... 433/215 |

OTHER PUBLICATIONS

Bell-Krotoski, JA, "Pocket filaments and specifications for the Semmes-Weinstein Monofilaments." 1990, J Hand Ther, Hanley & Belfus, p. 26-31.*

(Continued)

*Primary Examiner* — Max Hindenburg
*Assistant Examiner* — John Pani
(74) *Attorney, Agent, or Firm* — John B. Edel; Edel Patents LLC

(57) ABSTRACT

Testing instruments having a handle with a first handle portion that is substantially linear and a second handle portion wherein the handle is not substantially linear, a first monofilament, and a second monofilament wherein the first monofilament detachably connects to the second handle portion and wherein the second monofilament detachably connects to the second handle portion are disclosed herein. Further, methods of evaluating cutaneous sensory detection in which an instrument is held with a digit proximate to a position indicator, a skin area is contacted with a monofilament, sufficient pressure is applied to flex the monofilament, and the monofilament is withdrawn from the skin area.

7 Claims, 5 Drawing Sheets

(56) References Cited

OTHER PUBLICATIONS

Apelqvist, J. et al. "International consensus and practical guidelines on the management and the prevention of the diabetic foot." 2000. John Wiley & Sons, Ltd. Diabetes Metaolism Resarch and Reviews; 16 (Suppl 1). pp. S84-S92.*

U.S. Appl. No. 07/860,900, filed Mar. 31, 1992, Weinstein, et al.

Semmes, J; Weinstein, S; Ghent, L; and Teuber, HL: Somatosensory Changes after Penetrating Wounds in Man, Harvard Univ Press for Commonwealth fund, Cambridge, 1960, 5, 59-60.

Bell, JA: Sensibility testing, In Hunter, JM; Schneider, LH; Mackin, EJ; and Bell, JA (eds), Rehabilitation of the Hand, Phila, CV Mosby:1978, 278, 284-286.

Bell-Krotoski, JA; and Buford, WL, Jr.: The force/time relationship of clinically used sensory testing instruments, Phila, J Hand Ther, 1(2):1988, 78, 82.

Bell-Krotoski, JA; and Buford, WL., Jr.: The force/time relationship of clinically used sensory testing instruments: A revision and update, J of Hand Ther, 10(4):1997, 306.

Bell-Krotoski, JA; and Tomancik, E: The repeatability of testing with Semmes-Weinstein Monofilaments; the Amer Soc of Hand Therapists; J Hand Surg, 12A, No. 1, 1987, 161.

Bell-Krotoski, JA: Light touch-deep pressure testing using Semmes-Weinstein Monofilaments, In Hunter et al (eds), Rehabilitation of the Hand, Phila, C.V.Mosby, 1990, 591.

Bell-Krotoski, JA: Pocket filaments and specifications for the Semmes-Weinstein Monofilaments, J Hand Ther, Hanley & Belfus, 3: 26-30, 1990, 27, 29.

Bell-Krotoski, JA; Fess, EE; Hiltz, D; and Figarola, J: Threshold detection and Semmes Weinstein Monofilaments: A comparative study, J Hand Ther, 8: 1995, 157-161.

Weinstein, S: Fifty years of somatosensory research: from the Semmes-Weinstein Monofilaments to the Weinstein Enhanced Sensory Test; J Hand Ther, Hanley & Belfus 6:1993, 18.

Von Prince, K; and Butler, B: Measuring sensory function of the hand in peripheral nerve injuries, American J Occup Ther, 21:1967, 390, 391, Table 3.

* cited by examiner

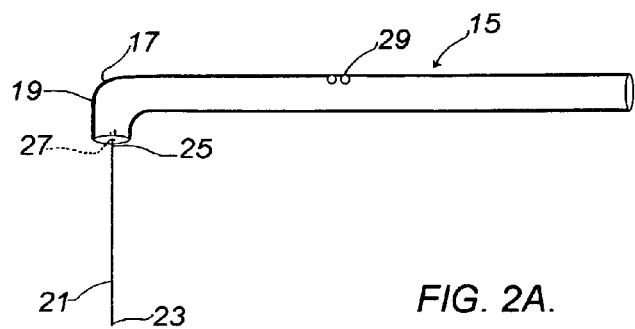
FIG. 2A.
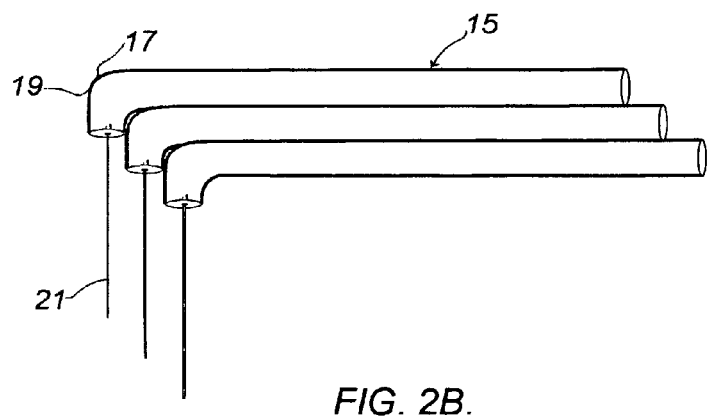
FIG. 2B.
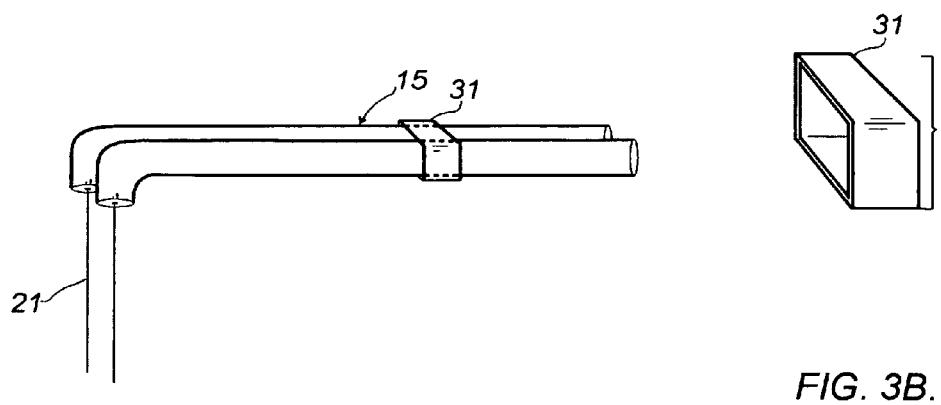
FIG. 3A.
FIG. 3B.

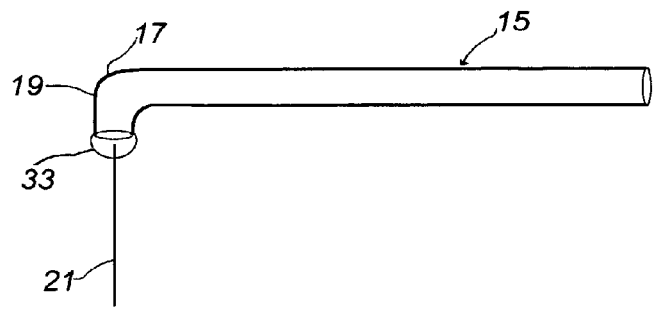
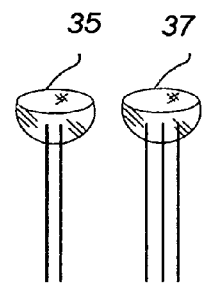
FIG. 4A.
FIG. 4B.
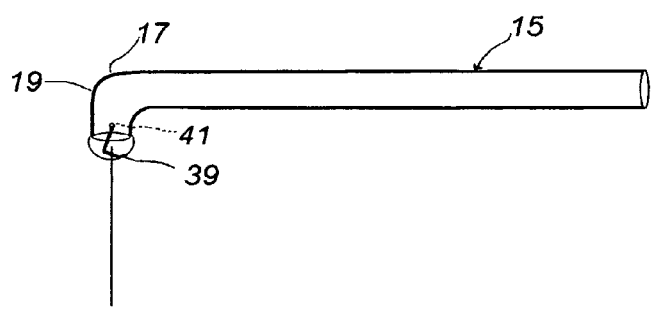
FIG. 4C.
FIG. 4D.
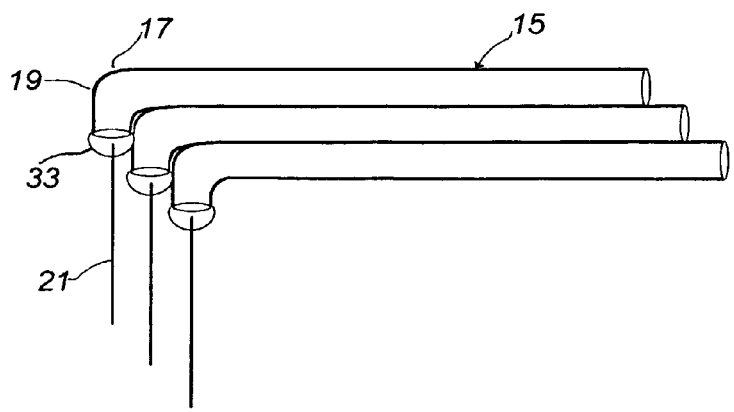
FIG. 4E.

CUTANEOUS SENSORY DETECTION

A testing instrument described herein may comprise a handle that comprises a first handle portion that is substantially linear and a second handle portion wherein the handle as the whole is not substantially linear; a first monofilament having a first diameter; and a second monofilament having a second diameter; wherein the first monofilament is arranged and configured to detachably connect to the second handle portion; wherein the second monofilament is arranged and configured to detachably connect to the second handle portion. In a related embodiment of the testing instrument, the first monofilament may be a first color, the second monofilament may be a second color that is distinct from the first color.

A testing instrument described herein may comprise a handle, a first monofilament having a first diameter; a second monofilament having a second diameter; a light; and a connection point for connecting a monofilament selected from the first monofilament and the second monofilament to the handle. In a related embodiment, the first monofilament is connected to the handle at the connection point and the first monofilament is arranged and configured to flex freely and without obstruction upon the contacting of that monofilament with a test subject.

A method of evaluating cutaneous sensory detection as described herein may comprise providing an instrument comprising a first monofilament, a light, a handle, and a position indicator on the handle; holding the instrument with a digit proximate to the position indicator; contacting a skin area with the first monofilament; applying sufficient pressure to flex the first monofilament; and withdrawing the first monofilament from the skin area. In a related method, the evaluation further comprises removing the first monofilament from the handle and attaching a second monofilament to the handle. In a further related method, the first monofilament is the only portion of the instrument that contacts the skin area during the contacting of the skin area with the first monofilament.

Embodiments disclosed herein may be used for testing directed to peripheral nerve evaluation, the evaluation of cutaneous sensory detection by the peripheral nervous system and the central nervous system. Sensitive repeatable measurement and quantification of early abnormality is important for early treatment intervention aimed at restoring normal nerve function, or maintaining remaining nerve function. Detection of more advanced abnormality is important to help prevent injury and amputations. Without special care and treatment, patients with peripheral nerve impairment who use hands and feet in daily life activities can have repetitive damage to skin and soft tissue resulting in injuries and amputations. Patients having ailments or injuries such as carpal tunnel or entrapment syndromes, work related injuries, repetitive stress syndromes, congenital neuropathies, and diseases such as diabetes and leprosy may be aided by the tests and equipment disclosed herein.

In an embodiment of the invention, nylon is used to evaluate skin sensitivity. Nylon has little humidity absorption, has an indefinite shelf life, and has repeatable bend and recovery elastic physical properties making it ideal for the cutaneous sensory detection test. In another embodiment of the invention, nylon monofilament of increasing diameters provide a range of repeatable test stimuli application forces suitable for cutaneous sensory testing.

In an embodiment of the invention, nylon monofilament, or material with similar physical properties, is applied perpendicular to the skin surface of the subject until the monofilament bends and exerts its desired force of application for testing. The nylon monofilament bends when applied to the skin, achieves a peak force immediately in application, and holds peak force until lifted, when it again becomes straight, and application force becomes zero. The force of application applied by a device is important for test accuracy and validity. Accuracy of the monofilament test for cutaneous sensory detection threshold is dependent both upon the properties of material being used as a stimulus, and the proper application of the stimulus monofilament tip for testing of subjects. Unseen vibration, which is not easily appreciated by an examiner's sight, will be detected by sensitive sensory end-organ receptors of the peripheral nerves in the skin of the patient being tested, and can change the results of the test. The elastic properties of nylon help absorb the vibration of the examiner's hand. Normal subjects are so sensitive they can feel light "puffs of air" on their skin. The control enabled by the elasticity of the monofilaments can help quantify differences even among normal subjects at this sensitive level of detection.

In an embodiment of the invention, the monofilaments and testing devices are designed to resist breakage of the monofilament. If only one monofilament is broken in any set of increasing monofilament diameters, an entire test set can be rendered incomplete, e.g. where monofilaments are used in a "hand and body," "face," or "foot" screen set, or in a nerve status "screening" or "normative testing" set requiring more than one monofilament size. Clinics doing testing often only have one set, or two sets available at any one time.

In an embodiment of the invention, the monofilaments are detachable from the handle such that individual monofilaments may be replaced without replacing the handle. This feature allows for monofilaments that are disposable in nature enhancing test cleanliness and providing an additional level of safety especially for patients with resistive diseases such as TB and HIV.

In another embodiment of the invention, the color is used to identify monofilament diameter or size. This color coding improves recognition by the examiner of a given diameter size monofilament in a device, facilitates several monofilament sizes being able to be put into one handle, and is frequently used in various versions of the monofilaments test today.

In an embodiment of the invention, the monofilament is colored or illuminated or both to enhance visibility of the monofilament assuring the monofilament and its tip are visible to the examiner at all times.

In an embodiment of the invention, the stimulus tip is rounded. With such a change, normative studies for blunt cut version would not apply to the rounded stimulus tip embodiment.

In an embodiment of the invention, the angle of the monofilament to the rod handle is 90°. Further, application of the monofilament to the skin area being tested may be perpendicular to better allow for the stimulus application being made in a smooth and consistent fashion. Still further, the distance from the monofilament to the examiner's holding position on the handle should be consistent, so as to minimize differences in the amount of examiner hand vibration, thus improving the repeatability of the stimulus.

In another embodiment, the monofilaments are made from pure nylon, extruded with controlled humidity in straight lengths during manufacture. Diameter and length of the nylon monofilaments are in specifications are specified by size and force.

In an embodiment of the invention, the monofilaments are cut such that they do not have sharp edges.

In another embodiment of the invention, two or more monofilaments may be attached to the handle for concurrent stimulation with preselected force of application.

In certain embodiments, the handle may have a curved handle design which decreases the likelihood of monofilament damage because the side of the handle having the monofilament is readily apparent from the end in the handle. Thus, the hard to see and easily damaged monofilaments should have infrequent incident of the rod handle being inadvertently laid down upon the monofilament. Further, the easy assembly, disassembly, and reassembly of the components of the device allowing for the safer handling of monofilaments, decreasing the likelihood that those monofilaments will be damaged.

In an embodiment of the invention, the handle of the device contains a mark, a rest, or other indication provides guidance as to where to hold the device. In a method utilizing that embodiment, the examiner's index finger is placed on the side opposite the monofilament at the indication encouraging consistency in the examiner's holding and application of the device.

In an embodiment of the invention, a variety of monofilament replacement disks or other connecting device are provided as an intermediate piece between the monofilament and the handle such that the disks can be interchanged with other disks to provide additional or alternative monofilaments as a source of stimulus. In an embodiment of the invention, monofilament replacement disks are provided such that damaged monofilament can quickly and easily be replaced. In an alternate embodiment, monofilament replacement disks are disposed of and replaced when dirty or once used. The disks may be pre-embedded with a monofilament of a given diameter size, and length, enabling the monofilaments to be quickly and easily replaced or interchanged by an examiner without replacing an entire device, or disassembling a device.

Embodiments providing either a light or a curved handle or both enhance test accuracy by allowing for enhanced detection of problems associated with testing. For example, the bent handle allows for easier identification of errors associated with applying the monofilament to skin when the monofilament is not perpendicular to the skin. Such applications can lead to errors when the person administering a test fails to detect slippage of the monofilament across the skin surface. The curve and extension of the handle enables the attached light source to transmit through the clear light-conducting handle, to be bent by the curve to illuminate the perpendicular monofilament test stimulus, its application tip, and a skin area of the subject tested in embodiments with or without the clear disk attachment. Recognizing errors is further enhanced by the use of the light to illuminate the examination area. Because embodiments having a light, a curved handle, or both aid in the detection of misapplications of the monofilament, more misapplications can be disregarded resulting in more accurate test results In an embodiment of the invention, cool light is provided to the test area illuminating the monofilament during the test. In a related embodiment, the cool light is provided indirectly through the handle, illuminating the test stimulus, the monofilament member, and the clear disk containing the monofilament during the test. Such embodiments avoid the undesired effect using a lamp over the skin area being tested. That direct light of a lamp can elevate the skin temperature of the area being tested by several degrees F. In a related embodiment, temperature is measured and maintained at the ambient temperature of the room and at a constant level during testing and repeat testing. Such control improved repeatability because it is known that nerves conduct faster when warmer than when cold, and because heating of the monofilament several degrees can change its degree of stiffness and therefore degraded the accuracy of intended force of application.

In one embodiment, the light of the device is sufficient to illuminate the skin area, but dim enough to avoid glare. In a related embodiment, the light is sufficient to conduct the tests in low light and at night.

The replaceable monofilaments found in many embodiments of the invention are susceptible to being placed in a relatively small box or container allowing for easier transfer, storage, and placement in the examination area.

The handle design of the embodiments disclosed herein allows for the compact storage of any variety of monofilaments and a handle in a nested arrangement in a nested arrangement in a small box or case.

In an embodiment of the invention, an outline, or map of skin areas is prepared such that changes in cutaneous sensory detection can be monitored in areas which are known to be innervated by specific nerves.

In an embodiment of the invention, records of force of application recognized by the subject are made in either a full or abbreviated version of a sensory test to produce detailed and specific maps of peripheral nerve abnormalities.

In an embodiment of the invention, monofilaments representing various cutaneous sensory detection threshold levels were consistently color coded for specific force recognition level. Test stimulus should be applied as carefully and precisely as possible, particularly avoiding areas of wounds or sutures.

In an embodiment of the invention, a versatile handle is provided for a visible monofilament stimulus whereby several diameter sizes can be grouped safely together and be readily available for clinical testing by an examiner in a small box or packet, with replacement monofilaments on hand and readily interchangeable as needed to assure a test is accurate, safe, and more versatile for clinical use in patients, or research into variations of optimal sensory test design. In another embodiment, a simple device handle design that protects the monofilament test stimulus with as few moving parts as possible provides for the versatility needed when the device is used in patient testing.

One embodiment includes a functional handle, means for replaceable monofilament, and option for a lighted monofilament stimulus whereby several devices of same or different diameter sizes can be safely grouped together and be readily available for clinical testing by the examiner in a small box or packet. Replacement monofilaments can be on hand and readily interchangeable during testing as needed to assure the test is both accurate and safe for clinical use in patients. The addition of the curve and extension to the handle protects the monofilament where it is attached to the handle. If inadvertently laid down incorrectly, the handle falls on its side or back, not on the monofilament. If dropped, the device lands on its back or side rather than the side to which the monofilament is secured. The curve and extension in handle design helps prevent the handle from being laid down on the monofilament, and the monofilament from being laid down upon itself and damaged. The curve serves the purpose of letting the examiner immediately recognize the correct orientation of the handle. The curve and extension in handle design prevents one device when grouped or nested together from shearing off the monofilament of a neighboring instrument. This feature is present regardless of whether the replaceable disk attachment is present. The replaceable disk serves as an additional cushion and shield for the monofilament, and fits into the handle curve and extension of a neighboring device when assembled. Monofilament devices in the new design can be secured in the smaller box or case for coat-pocket, tabletop, or other form of display, and are safer if the box is dropped.

BRIEF DESCRIPTION OF THE DRAWINGS

FIG. 2A shows an embodiment of an instrument including a handle and a monofilament.

FIG. 2B shows several instruments nested together.

FIG. 3A shows two new device handles connected.

FIG. 3B is a close up view of a connector attachment.

FIG. 4A shows an embodiment of an instrument having a replacement disk.

FIG. 4B shows two variations of embodiments having a replacement disk.

FIG. 4C shows an embodiment of an instrument having a replaceable disk and a clip.

FIG. 4D is a close up view of the clip.

FIG. 4E shows a series of instruments with replaceable disks in a nested arrangement.

DETAILED DESCRIPTION

Figure 1A:
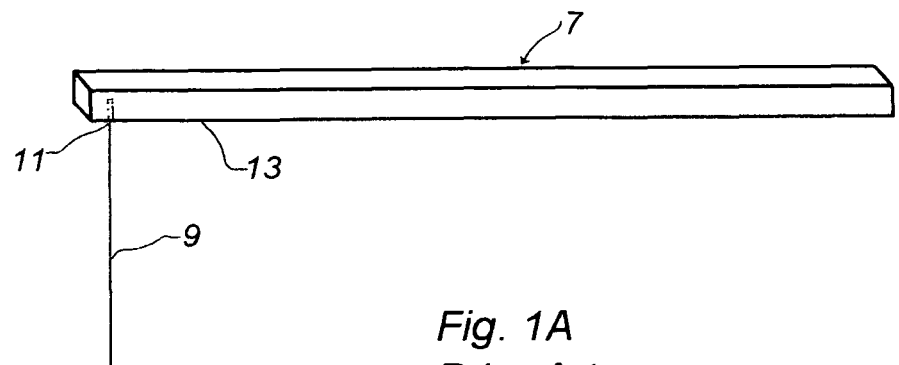
FIG. 1A-1B show prior art monofilament designs including damaged monofilament in FIG. 1B and FIG. 1C.

Referring now to FIG. 1A of the drawings, an instrument from the prior art is made up of a Straight rod handle 7 and a Monofilament member 9 with the Monofilament exit from straight rod handle 11 located at the Monofilament end of straight rod handle 13. Monofilament member 9 is most susceptible to damage at Monofilament exit from straight rod handle 11.

Figure 1B:
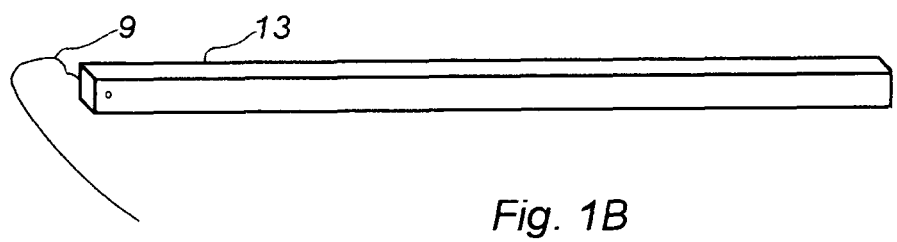

Referring now to FIG. 1B of the drawings, Monofilament member 9 is shown as a damaged monofilament, such damage being the typical of the damage that occurs with thinner monofilaments when the instrument is laid down on Monofilament end of straight rod handle 13 such that Monofilament member 9 contacts the surface.

Figure 1C:
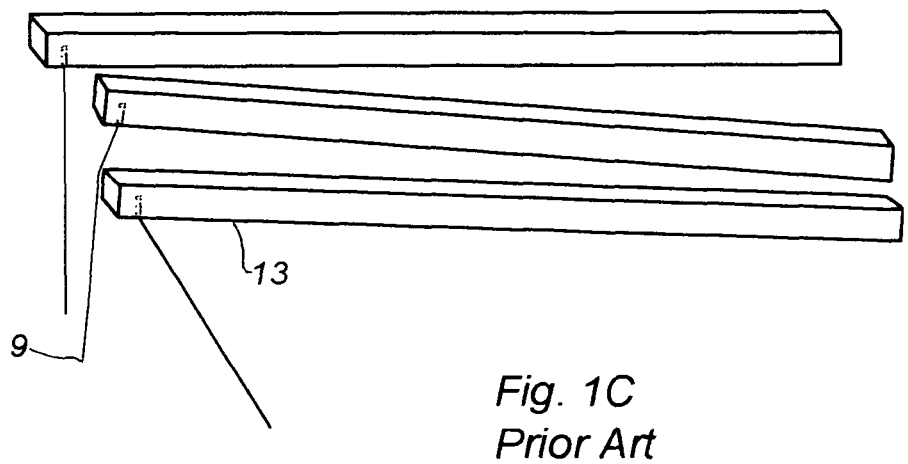

FIG. 1C shows a set of prior art instruments as they are sometimes stored together. When stored in this configuration, Monofilament member 9 is sometimes damaged by the Monofilament end of straight rod handle 13 of an adjacent instrument.

Now referring to FIG. 2A of the drawings, Handle 15 comprises a long body, a Handle curve 17 and a Handle curve extension 19 which terminates in a Handle hole for monofilament 27. Handle curve extension 19 functions to protect Monofilament 21 from damage. Handle 15 contains a Handle position indicator 29 for consistent placement of the examiner's index finger on the handle, at a distance from the monofilament. Monofilament 21 protrudes from Handle curve extension 19 with Monofilament stimulus tip end 23 located opposite Monofilament handle end 25.

FIG. 2B shows three instruments nested together in a configuration that protects the Monofilaments 21. The instrument may be stored in this configuration. Each of Handles 15 are arranged adjacent to each other such that Handle curves 17 are nested within each other and such that Handle curve extensions 19 are also adjacent to each other. This configuration allows for each of the Monofilaments 21 to be at a safe distance from each other and from the Handles 15 of other instruments.

FIG. 3A shows an embodiment in which two instruments are used in together. In this embodiment, Handles 15 are held adjacent to one another by Two handle adapter connector 31. In this embodiment, the instrument may be used to test with two Monofilaments 21 simultaneously.

FIG. 3B shows a close up of one embodiment of Two handle adapter connector 31.

FIG. 4A shows another embodiment of the instrument in which Replaceable monofilament disk attachment 33 is used. In this embodiment, Handle 15, Handle curve 17, and Handle curve extension 19 are configured as previously discussed. However, Replaceable monofilament disk attachment 33 exists as an intermediate element between Handle curve extension 19 and Monofilament 21. Replaceable monofilament disk attachment 33 is pre-embedded with the monofilament of preselected diameter and size such that Replaceable monofilament disk attachment 33 and Monofilament 21 may be added together onto the terminal end of Handle curve extension 19. The present embodiment allows for easy interchange of Replaceable monofilament disk attachments 33 and Monofilaments 21 on a single Handle 15.

FIG. 4B shows two examples of a variety of possible alternatives for replaceable monofilament disk attachments, namely Two point testing monofilament disk attachment 35 which is useful for two point monofilament testing and Three point testing monofilament disk attachment 37 which is useful for three point monofilament testing. These testing configurations are replaceable on a single Handle 15 as described above.

FIG. 4C shows an embodiment comprising Handle 15, Handle curve 17, and Handle curve extension 19. The embodiment shown in FIG. 4C further comprises, a set of Disk attachment clip holes 41 positioned near the end of Handle curve extension 19 such that Disk attachment clip 39 may be inserted into Disk attachment clip holes 41 securing Replaceable monofilament disk attachment 33 (not labeled) to Handle 15 at Handle curve extension 19.

FIG. 4D shows a close up of Disk attachment clip 39.

FIG. 4E shows three instruments nested together in a configuration that protects the Monofilaments 21. The instrument may be stored in this configuration. Each of Handles 15 are arranged adjacent to each other such that Handle curves 17 are nested within each other, such that Handle curve extensions 19 are adjacent to each other, and such that the pairs of Replaceable monofilament disk attachments 33 and Monofilaments 21 are separated from the other pairs of Replaceable monofilament disk attachments 33 and Monofilaments 21. This configuration also allows for each of the Monofilaments 21 to be at a safe distance from each other and from the Handles 15 of other instruments.

Figure 5A:
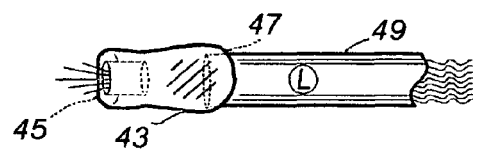
FIG. 5A shows an adapter attachment for use with a light-emitting source.

FIG. 5A shows an embodiment in which Light-emitting source 49 transmits light through a Light attachment adapter 43 that has a Adapter handle receptacle 45 and a Adapter light receptacle 47. Handles of various embodiments of the invention capable of transmitting light to the testing area may be connected to Adapter handle receptacle 45.

Figure 5B:
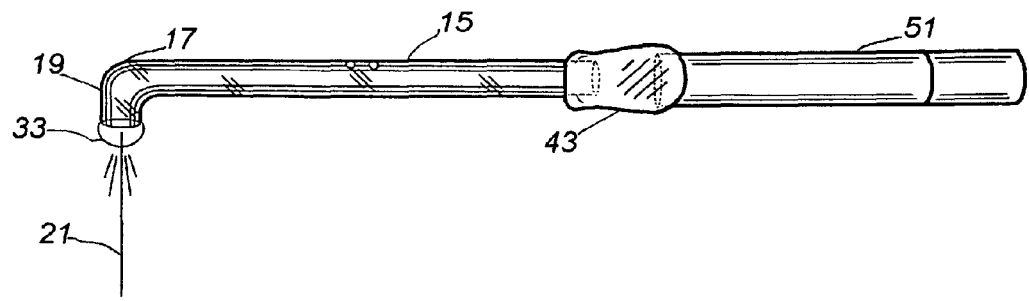
FIG. 5B shows an embodiment of an instrument including a light source.
Figure 6:
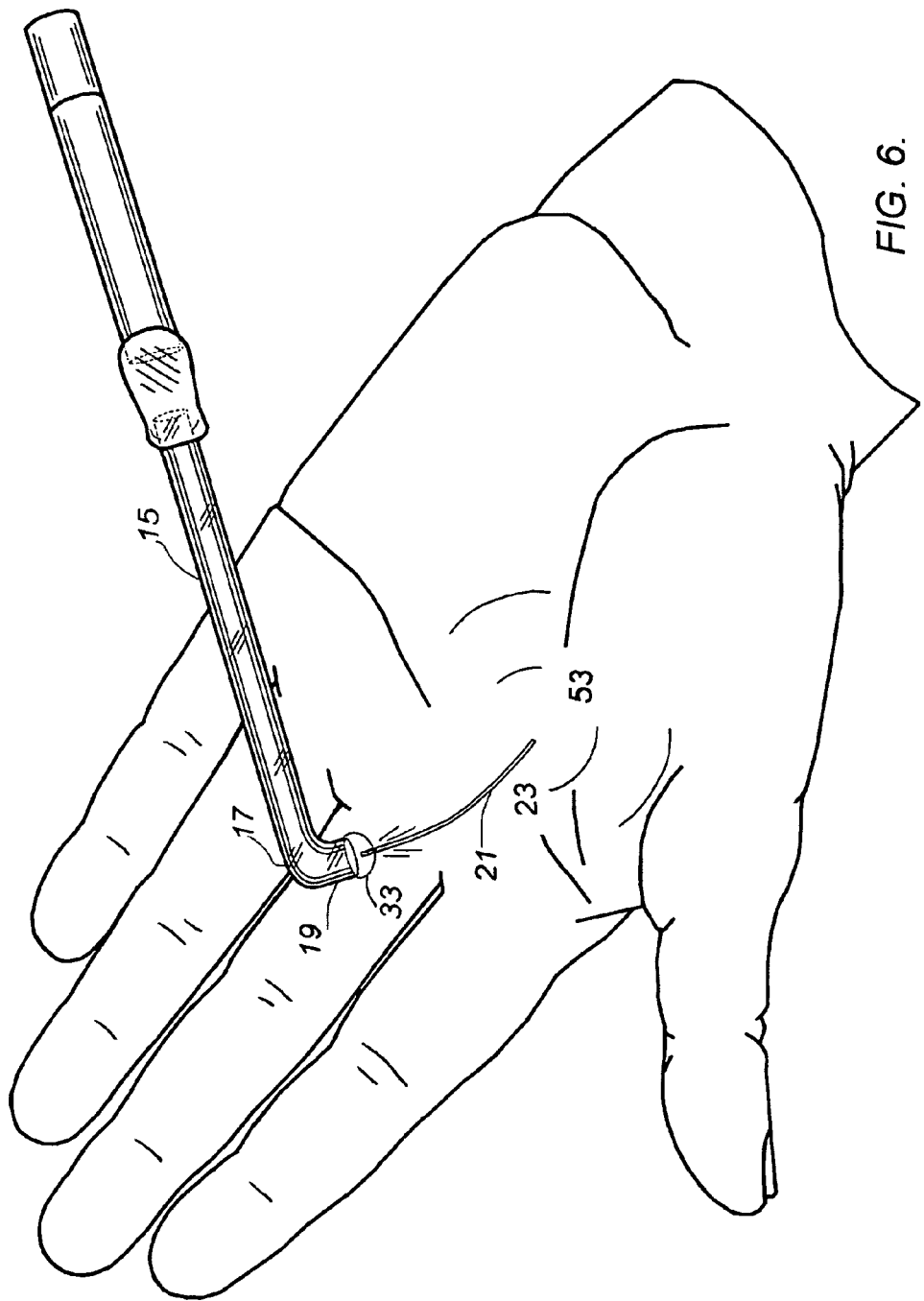
FIG. 6 shows an instrument testing the hand of a human subject.

FIG. 5B shows an embodiment utilizing the Handle 15, Handle curve 17, Handle curve extension 19, and Monofilament 21 configuration attached to a Battery powered light source 51 by Light attachment adapter 43. This configuration allows for light to be transmitted through Handle 15 to a test area. Such a configuration could be powered by a small conventional battery powered light from one of many known light sources. FIG. 6 shows an embodiment substantially configured in the form described in the treatment of FIG. 5B utilized in the testing of a human hand. In this embodiment, a portion of the hand represented by Lighted test area 53 is contacted by Monofilament stimulus tip end 23 of Monofilament 21 to provide the test stimulus. Light is transmitted through Handle 15, Handle curve 17, Handle curve extension 19, and Replaceable monofilament disk attachment 33 to illuminate Lighted test area 53.

There are, of course, other alternate embodiments which are obvious from the foregoing descriptions of the invention, which are intended to be included within the scope of the invention, as defined by the following claims.

I claim:

1. A sensory testing device comprising:
   a. an elongate body comprising a first end, a second end and a middle;
   b. a first monofilament attached to the elongate body;
   c. a light source securely receiving and holding and removably attached to the elongate body wherein the light source is configured to produce a quantity of light and direct a portion of the quantity of light into the first end of the elongate body and out of the second end of the elongate body thereby illuminating the first monofilament;
   d. wherein the first monofilament has a first monofilament attachment end and a first monofilament stimulus tip located opposite the first monofilament attachment end;
   e. wherein the first monofilament attachment end is attached to the elongate body at the second end;
   f. wherein the elongate body is bent at the second end;
   g. wherein the elongate body is arranged and configured to illuminate the first monofilament stimulus tip;
   h. wherein the first monofilament is arranged and configured for administration of a cutaneous sensory detection test;
   i. wherein only one, two, or three monofilaments are attached to the elongate body.

2. The sensory testing device of claim 1 further comprising a position indicator located on the middle of the elongate body.

3. The sensory testing device of claim 1 further comprising a second monofilament having a second monofilament attachment end and a second monofilament stimulus tip wherein the first monofilament attachment end is removably attached to the elongate body at the second end and wherein the second monofilament is interchangeable with the first monofilament.

4. The sensory testing device of claim 1, further comprising an intermediate piece constructed of a clear material wherein the intermediate piece attaches the first monofilament attachment end to the elongate body at the second end.

5. The sensory testing device of claim 1, further comprising a second stimulus monofilament adjacent to the first monofilament wherein the second stimulus monofilament extends alongside to the first monofilament.

6. A sensory testing device comprising:
   a. a first elongate translucent plastic rod having a first end, a second end, and a curved portion between the first end and the second end, wherein the curved portion is adjacent to the second end and wherein the first end is oriented transverse to the second end;
   b. a first translucent attachment piece attached to the second end of the first elongate translucent plastic rod;
   c. a first monofilament, having a first monofilament diameter, attached to the first translucent attachment piece;
   d. a second elongate translucent plastic rod having a first end, a second end, and a curved portion between the first end and the second end, wherein the curved portion is adjacent to the second end and wherein the first end is oriented transverse to the second end;
   e. a second translucent attachment piece attached to the second end of the second elongate translucent plastic rod;
   f. a second monofilament, having a second monofilament diameter, attached to the second translucent attachment piece;
   g. a battery powered light source configured to securely receive and hold the first end of the first elongate translucent rod;
   h. wherein the first monofilament diameter is different than the second monofilament diameter;
   i. wherein the battery powered light source is arranged to produce a quantity of light;
   j. wherein the battery powered light source is arranged such that a portion of the quantity of light travels down the first elongate translucent plastic rod through the curved portion of the first elongate translucent plastic rod illuminating the first monofilament when the first elongate translucent plastic rod is held by the battery powered light source;
   k. wherein the first elongate translucent plastic rod and the second elongate translucent plastic rod are sized and configured such that they may be paired in a nesting relationship separate from the battery powered light source protecting both the first monofilament and the second monofilament from damage;
   l. wherein the first elongate translucent plastic rod, the first translucent attachment piece, the first monofilament, and the battery powered light source are configured for administration of a cutaneous sensory threshold test when the first elongate translucent plastic rod is held by the battery powered light source.

7. A method of evaluating cutaneous sensory detection comprising:
   a. providing a sensory testing device comprising:
      i. a first elongate translucent plastic rod having a first end, a second end, and a curved portion between the first end and the second end, wherein the curved portion is adjacent to the second end and wherein the first end is oriented transverse to the second end;
      ii. a first translucent attachment piece attached to the second end of the first elongate translucent plastic rod;
      iii. a first monofilament, having a first monofilament diameter, attached to the first translucent attachment piece;
      iv. a second elongate translucent plastic rod having a first end, a second end, and a curved portion between the first end and the second end, wherein the curved portion is adjacent to the second end and wherein the first end is oriented transverse to the second end;
      v. a second translucent attachment piece attached to the second end of the second elongate translucent plastic rod;
      vi. a second monofilament, having a second monofilament diameter, attached to the second translucent attachment piece;
      vii. a battery powered light source configured to securely receive and hold the first end of the first elongate translucent rod;
      viii. a position indicator on the first elongate translucent plastic rod adjacent to the first end of the first elongate translucent plastic rod;
      ix. wherein the first monofilament diameter is different than the second monofilament diameter;
      x. wherein the battery powered light source is arranged to produce a quantity of light;

xi. wherein the battery powered light source is arranged such that a portion of the quantity of light travels down the first elongate translucent plastic rod through the curved portion of the first elongate translucent plastic rod illuminating the first monofilament when the first elongate translucent plastic rod is held by the battery powered light source;

xii. wherein the first elongate translucent plastic rod and the second elongate translucent plastic rod are sized and configured such that they may be paired in a nesting relationship separate from the battery powered light source protecting both the first monofilament and the second monofilament from damage;

xiii. wherein the first elongate translucent plastic rod, the first translucent attachment piece, the first monofilament, and the battery powered light source are configured for administration of a cutaneous sensory threshold test when the first elongate translucent plastic rod is held by the battery powered light source;

b. illuminating the first monofilament with the battery powered light source;

c. contacting a skin area with the first monofilament;

d. applying sufficient pressure at the position indicator with an index finger to flex the first monofilament; and e. withdrawing the first monofilament from the skin area.

* * * * *